United States Patent
Gladnick

(10) Patent No.: US 7,782,513 B1
(45) Date of Patent: Aug. 24, 2010

(54) FAST VARIABLE ANGLE OF INCIDENCE ILLUMINATION FOR A MACHINE VISION INSPECTION SYSTEM

(75) Inventor: Paul G. Gladnick, Seattle, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 0 days.

(21) Appl. No.: 12/512,915

(22) Filed: Jul. 30, 2009

(51) Int. Cl.
*G02B 26/08* (2006.01)

(52) U.S. Cl. .............. 359/196.1; 359/212.1; 359/212.2; 359/223.1; 362/326; 362/341; 356/237.2

(58) Field of Classification Search ... 359/196.1–198.1, 359/209.1–214.1, 223.1, 226.1, 385, 387
See application file for complete search history.

(56) References Cited

U.S. PATENT DOCUMENTS

| | | | |
|---|---|---|---|
| 4,622,625 A | 11/1986 | Becker | |
| 5,467,150 A | 11/1995 | Isogawa | |
| 5,690,417 A | 11/1997 | Polidor | |
| 5,775,790 A * | 7/1998 | Ohtake | 362/18 |
| 5,897,195 A | 4/1999 | Choate | |
| 6,179,439 B1 * | 1/2001 | Choate | 362/247 |
| 6,614,596 B2 | 9/2003 | Gladnick | |
| 6,857,762 B2 | 2/2005 | Shimokawa | |
| 2002/0071272 A1 * | 6/2002 | Tenmyo | 362/223 |
| 2005/0083519 A1 * | 4/2005 | Maeda et al. | 356/237.2 |

* cited by examiner

*Primary Examiner*—James Phan
(74) *Attorney, Agent, or Firm*—Christensen O'Connor Johnson Kindness PLLC

(57) ABSTRACT

A fast variable angle of incidence illumination configuration for a machine vision inspection system, including: a light source that directs a beam along a first optical path portion; a beam steering arrangement that receives the beam and steers it along a second optical path portion; and a beam deflecting arrangement including a plurality of surface portions arranged at respective angles of incidence to receive the beam and deflect it along a third optical path portion to a field of view. The beam steering arrangement includes different surfaces that provide either narrow or wide divergence of the beam toward the deflecting arrangement. The illumination configuration allows for fast adjustment of not only the illumination angle of incidence but also the range of angles (narrow or wide) about the nominal angle. The illumination configuration is particularly suitable for use with light provided by a high-intensity remote light source.

15 Claims, 8 Drawing Sheets

FAST VARIABLE ANGLE OF INCIDENCE ILLUMINATION FOR A MACHINE VISION INSPECTION SYSTEM

BACKGROUND

Workpiece feature-specific illumination is often necessary in precision machine vision inspection systems to accentuate an edge or other feature in an inspection image. Many such systems including lighting systems are capable of providing relatively focused coaxial illumination through a camera or microscope lens, "stage light" from behind a workpiece to create an accurate silhouette image, and/or diffuse illumination. Some lighting systems include arrangements that are capable of projecting light onto the workpiece at an adjustable angle of incidence relative to an axis which is normal to the nominal object plane that is imaged. In many conventional vision systems, the axis normal to the nominal object plane is parallel to, or coincides with, the optical axis of the vision system. Light projected at a selected angular range and/or angle of incidence between 0° and 90° may improve the contrast of edges in the image and/or may more clearly illuminate textured surfaces. Typically, such light sources have a selectable range for the angle of incidence varying between approximately 10° and 70°. Such a range is relatively broad so as to have the capability to enhance image contrast for a variety of types of workpiece features.

Enhanced image contrast for a feature is important because image processing algorithms that perform edge-finding and surface autofocus operations are often designed to detect locations that are associated with maximum grayscale gradients in a inspection image. Thus, grayscale gradients are of particular significance in workpiece inspection images, and these "gradient signals" are enhanced when the image contrast is enhanced.

Some lighting systems can also adjust or select the radial direction of the lighting about an optical axis, for example, by using lighting elements arranged around the optical axis in a "ring light" configuration that includes addressable sectors or quadrants. The field of view of a camera can be illuminated by any combination of sectors or quadrants of such a generally ring-shaped lighting system. The intensity level and/or color content of the light source can be coordinated with the angle of incidence and the radial direction of the light source to optimize the illumination of a workpiece edge.

In one type of lighting system, light emitting diodes (LEDs) are arranged in an annular pattern to surround the optical axis of the vision system. An exemplary lighting system of this type is disclosed in U.S. Pat. No. 5,897,195, issued to Choate (hereinafter "the '195 patent"). The '195 patent discloses an oblique LED illuminator device made from a cylindrical or truncated-conical array of LEDs. The array of LEDs produces collimated light beams and directs them to the inclined surfaces of an annular-shaped Fresnel-like diffuser, which is coaxially arranged radially inward of the array of LEDs. The Fresnel-like diffuser refracts and directs LED light beams onto the surface of a workpiece at various angles of incidence. The Fresnel-like diffuser includes a plurality of annular, prism-shaped projections which differ in shape depending upon the desired angle of incidence. To create a beam of light with a particular angular range and/or angle of incidence, a light beam is emitted from particular LEDs (e.g., one or more LEDs) to the associated prism-shaped projection (s) within the Fresnel-like diffuser, which redirects the light beam onto the workpiece with the particular angular range and/or angle of incidence.

Strobe lighting is increasingly used in precision machine vision inspection systems in order to provide accurate unblurred images while moving the workpiece continuously, thereby improving inspection throughput. While the lighting system of the '195 patent allows for fast switching among various LEDs and hence among various angles of incidence, the relatively low optical energy output of LED's limits the illumination intensity, which extends the exposure time required for a given image exposure (e.g., to tens or hundreds of microseconds, or more). Longer image exposure times generally require slower workpiece motion in order to limit workpiece blur to an acceptable level. Therefore, the system of the '195 patent limits inspection throughput because it limits allowable workpiece motion speeds.

In another type of ring lighting system, LEDs and associated optical elements are selectively moved to achieve a desired angle of incidence. An example of this type of system is disclosed in U.S. Pat. No. 6,857,762, issued to Shimokawa et al. (hereinafter "the '762 patent"), which is incorporated herein by reference. The '762 patent discloses LEDs that are arranged generally annularly around an optical axis of the vision system. An annular reflector mirror is coaxially arranged radially outward of the annular LEDs, such that the light from the LEDs is directed at the reflector mirror and is reflected therefrom toward a focal point on the imaging plane at a specific angle of incidence. The reflector mirror has a convex surface having a varying radius of curvature, and is movable relative to the LEDs along the optical axis. Thus, a user can selectively move the reflector mirror relative to the LEDs such that the light from the LEDs will be reflected from a different position along the varying radius of curvature of the reflector mirror so as to illuminate a focal point on the imaging plane at a different angle of incidence. In this arrangement, the LEDs may be replaced with high-intensity light sources such as fiber optic cables used with a halogen lamp. Specifically, a number of fiber optic cables may be arranged such that first ends of the fiber optic cables receive light from a high-intensity light source, such as a halogen lamp, while the second ends of the fiber optic cables are arranged in an annular shape around the optical axis. The fiber optic cables, or sets of the fiber optic cables, can be individually controlled to project the high-intensity light from the light source onto the field of view of a camera at a desired angle of incidence based on a selective movement of the annular reflector mirror. While such a lighting system allows for adjusting the angle of incidence of a high-intensity illumination source, due to the mechanical movement of various parts involved, this adjustment may take tens or hundreds of milliseconds or more. Thus, adjustment of an angle of incidence cannot be performed as fast as in the case of the '195 patent, described above, which includes no moving parts. Therefore, the system of the '762 patent limits inspection throughput because the workpiece may have to be delayed at (or between) workpiece feature imaging positions while waiting for the lighting system configuration to be reconfigured to the particular configuration to be used for the next image.

A need exists for an illumination system configuration for use in a precision machine vision inspection system, which allows for inspection throughput increases by providing both very fast adjustment of the angular range and/or nominal angle of incidence of illumination, as well as the use of a high-intensity light source, such as a halogen lamp.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with various exemplary embodiments of the present invention, a fast variable angle of incidence illumination configuration is provided for use in a machine vision inspection system. The machine vision inspection system includes at least a first objective lens having an optical axis. The fast variable angle of incidence illumination configuration includes generally three elements: (a) a first light source configured to direct a light beam along a first optical path portion; (b) a beam steering arrangement configured to receive the light beam along the first optical path portion and steer the light beam along a second optical path portion; and (c) a beam deflecting arrangement that receives the light beam along the second optical path portion and deflects the light beam along a third optical path portion to illuminate a field of view of the objective lens. The beam deflecting arrangement includes a plurality of respective surface portions arranged at respective nominal angles of incidence relative to the optical axis, such as a plurality of respective strip-like arcuate faces arranged to reflect the received light at a plurality of respective angles of incidence. In one implementation, the transition between the respective surface portions may be readily distinguished. In another implementation, the transition between the respective surface portions may be gradual, such that each surface portion is distinguished primarily by its respective angle of incidence, rather than by an obvious physical boundary.

The beam steering arrangement of (b) includes generally three sub-elements: (i) at least one movable beam steering element and a controllable actuator that moves the movable beam steering element; (ii) at least a first beam steering surface portion that provides a first nominal divergence amount for the light beam along the second optical path portion, wherein the divergence amount is defined in a plane including the optical axis; and (iii) at least a second beam steering surface portion that provides a second nominal divergence amount for the light beam along the second optical path portion, wherein the divergence amount is defined in the plane including the optical axis.

The first nominal divergence amount corresponds to the light beam illuminating approximately a single respective surface portion of the beam deflecting arrangement, such that the fast variable angle of incidence illumination configuration illuminates the field of view from a narrow range of angles of incidence corresponding to the respective nominal angle of incidence of that single respective surface portion. In other words, the first nominal divergence amount results in a "narrow" light beam (e.g., a sheet-like arcuate or conical beam) illuminating the field of view.

The second nominal divergence amount corresponds to the light beam illuminating at least two respective surface portions of the beam deflecting arrangement, such that the fast variable angle of incidence illumination configuration illuminates the field of view from a broader range of angles of incidence that is broader than the narrow range of angles of incidence and that includes the respective nominal angles of incidence of the at least two respective surface portions. In other words, the second nominal divergence amount results in a "broader" light beam (e.g., a thick arcuate or conical beam) illuminating the field of view.

The beam steering arrangement of (b) is configured to provide the light beam along the second optical path portion with the first nominal divergence amount to different respective surface portions of the beam deflecting arrangement to illuminate the field of view from the narrow range of angles of incidence. In other words, the beam steering arrangement is configured to illuminate the field of view with a "narrow" light beam at different angles of incidence (e.g., at 30°, at 35°, at 40°, etc.). The beam steering arrangement is further configured to provide the light beam along the second optical path portion with the second nominal divergence amount to the at least two respective surface portions of the beam deflecting arrangement to illuminate the field of view from the broader range of angles of incidence. In other words, the beam steering arrangement is further configured to illuminate the field of view with a "broader" light beam that includes multiple angles of incidence (e.g., a "broader" light beam with angles of incidence ranging over any range between 10° and 70°.

Accordingly, the illumination configuration according to various embodiments of the present invention allows for fast adjustment of not only the nominal angle of incidence of illumination but also the range (narrow or broad) of angles of incidence included in the illumination. Furthermore, the illumination configuration readily permits use of a light source having high optical energy, such as a halogen lamp.

In accordance with one aspect of the present invention, the first and second beam steering surface portions (ii) and (iii) of the beam steering arrangement (b), and/or the respective surface portions of the beam deflecting arrangement (c) are reflective. In accordance with another aspect of the present invention, the respective surface portions of the beam deflecting arrangement (c) are refractive.

In accordance with a further aspect of the present invention, the beam steering arrangement (b) includes a fixed element that receives the light beam from the movable beam steering element (i) and outputs the light beam along the second optical path portion. The fixed element may include a plurality of different beam steering surface portions, and different beam steering surface portions output the light beam along the second optical path portion to different respective surface portions of the beam deflecting arrangement (c). For example, the fixed element includes the first and second beam steering surface portions (ii) and (iii).

In accordance with a still further aspect of the present invention, the plurality of fixed different beam steering surface portions include first and second sets of different beam steering surface portions, so as to illuminate the field of view of the objective lens at a first distance (on a first focal plane) and at a second distance (on a second focal plane), respectively, along the optical axis from the objective lens.

In accordance with another aspect of the present invention, the first and second beam steering surface portions (ii) and (iii) may be included in the movable beam steering element (i) and thus may be movable. The first beam steering surface portion may include a generally flat surface to produce a "narrow" light beam, while the second beam steering surface portion may include a generally semispherical surface to produce a "broader" light beam.

In accordance with yet another aspect of the present invention, the plurality of respective surface portions of the beam deflecting arrangement (c) include first and second sets of respective surface portions, which are configured to output the light beam along the third optical path portion to illuminate the field of view of the objective lens at a first distance (on a first focal plane) and at a second distance (on a second focal plane), respectively, along the optical axis from the objective lens.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
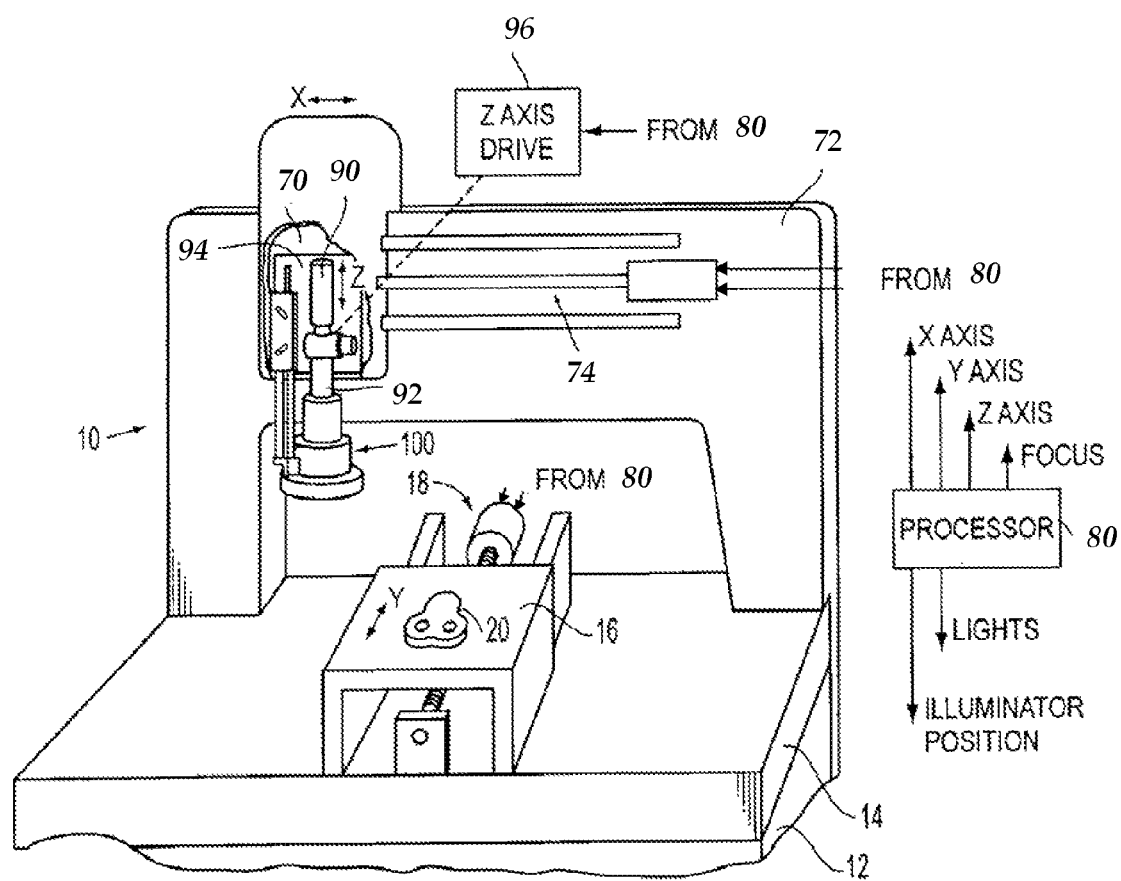
FIG. 1 is a perspective view, partially cut away, of a vision system incorporating an illumination configuration in accordance with various embodiments of the present invention.

FIG. 1 illustrates a machine vision inspection system (or "vision system") 10 suitable for incorporating a fast variable angle of incidence illumination configuration in accordance with various exemplary embodiments of the present invention. The vision system 10 includes a base console 12 having a table 14. A stage 16 is mounted on the table 14 in a movable manner in the Y direction relative to the table 14 under the control of a drive 18. The drive 18 includes a motor and lead screw. A vertically mounted camera 90 views a workpiece 20 to be inspected via an optical system 92 including an objective lens 23 (not shown in FIG. 1, but shown in FIG. 2). The stage 16 is movable to place the workpiece 20 at a desired position within the field of view of the camera 90.

The camera 90 is mounted on a Z-axis support 94 that is driven in the vertical direction by a Z-axis drive 36 so that the camera 90 can focus on particular regions and surfaces of the workpiece 20 that lie within the field of view. The camera 90 and the Z-axis support 94 are mounted on an X-axis carriage 70 that is in turn mounted on a vibration-free bridge 72 spanning the field of view above the stage 16. The carriage 70 is translated in the horizontal plane by a drive 74 comprising a motor and lead screw. The drives 18 and 74, as well as the Z-axis drive 36, are controlled by signals from a processor 80. The processor 80 is typically programmed to position the workpiece 20 at given X and Y axis positions relative to the camera 90 and also to focus the camera 90 on a particular level of the workpiece 20 along the Z axis. An illumination configuration 100 having elements concentric with the optical axis of the optical system 92 is mounted on the Z-axis support 94 together with the camera 90 and the optical system 92. The illumination configuration 100 is a fast variable angle of incidence illumination configuration according to various exemplary embodiments of the present invention. As shown in FIG. 1, the processor 80 controls the operation of the illumination configuration 100, such as the characteristics of the illuminating light, including its intensity and color ("LIGHTS"), as well as the illuminator's position ("ILLUMINATOR POSITION") including which quadrant(s) or section(s) of a circular illumination system is activated, at what angle(s) of incidence, etc.

Figure 2:
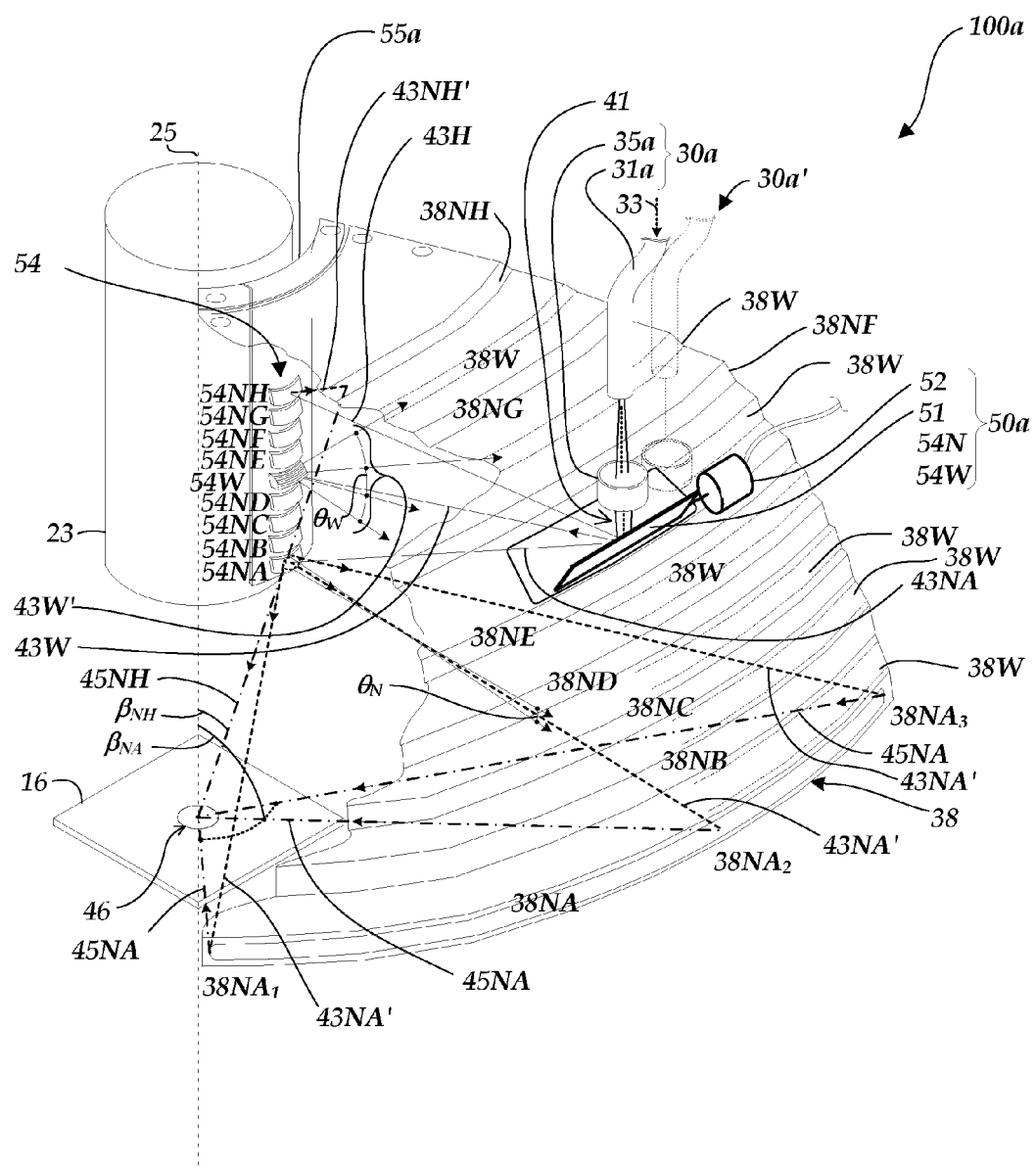
FIG. 2 is a perspective view, partially cut away, of an illumination configuration according to one embodiment of the present invention.
Figure 3:
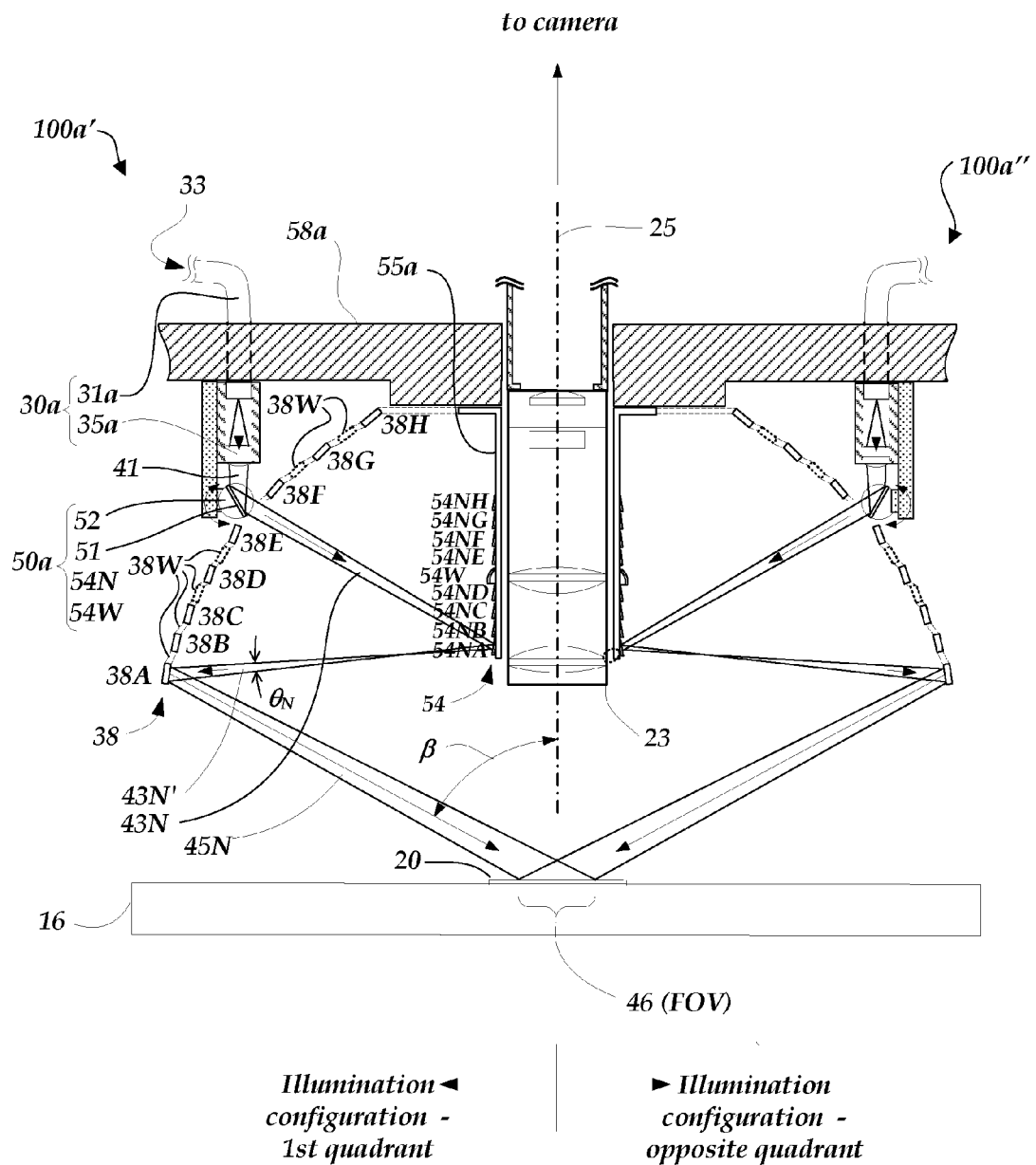
FIG. 3 is a cross-sectional view of the illumination configuration of FIG. 2 that is provided for one quadrant of a generally circular illumination system, which further includes the same illumination configuration in a mirror image provided for the opposite quadrant.

FIGS. 2 and 3 illustrate one embodiment of an illumination configuration 100a having a fast variable angle of incidence (the angle of incidence $\beta$, with or without subscript, see FIG. 3), formed in accordance with the present invention. The illumination configuration 100a is for use in a machine vision inspection system, which includes an objective lens 23 having an optical axis 25, and a stage 16 on which a workpiece to be inspected (not shown) is to be placed. For the purpose of clarity, illustration of the rest of the machine vision inspection system is omitted.

FIG. 2 is a perspective view of the illumination configuration 100a, while FIG. 3 is a cross-sectional view of the two of the same illumination configuration, 100a' and 100a", provided on the opposing sides of the objective lens 23 to respectively cover the first quadrant and the opposite quadrant of a generally circular illumination system. The illumination configurations 100a' and 100a" are configured and operated the same, except that they are mirror images of each other.

The illumination configuration 100a includes generally three elements: (a) a first light source 30a configured to direct a light beam along a first optical path portion 41; (b) a beam steering arrangement 50a configured to receive the light beam along the first optical path portion 41 and to steer the light beam along a second optical path portion 43 (which may have multiple segments); and (c) a beam deflecting arrangement 38 comprising a plurality of respective surface portions (e.g., the surface portions 38NA-38NH, and 38W's in the embodiment shown in FIG. 2) arranged at respective nominal angles of incidence relative to the optical axis 25 to receive the light beam along the second optical path portion 43 and deflect the light beam along a third optical path portion 45 to illuminate a field of view 46 approximately at the focal length of the objective lens 23 using a desired angle of incidence range at a respective nominal angle of incidence.

In the illustrated embodiment, the beam deflecting arrangement 38 includes respective surface portions 38NA-38NH arranged with alternating surface portions 38W. The respective surface portions 38NA-38NH are used to illuminate the field of view 46 with a narrow angle of incidence range (e.g., corresponding to ON) at respective nominal angles of incidence, and the surface portions 38W are used to illuminate the field of view 46 with a wide angle of incidence range (e.g., corresponding to $\theta W$), as will be more fully described below. In a numbering convention used herein, when reference numbers include an "N" they generally refer to elements that operate to provide a relatively narrower angle of incidence range, and when reference numbers include a "W" they generally refer to elements that operate to provide a relatively wider angle of incidence range. However, as will be clear from the overall description, in some cases elements may operate in both modes, regardless of the presence or absence of an N or W designator.

In the illustrated embodiment, the first light source 30a comprises optical fiber cable 31a (e.g., a fiber or fiber bundle)

and further comprises a beam shaping lens 35a which transmit light 33 generated from a remote light source. The beam shaping lens 35a shapes and focuses the light beam along the first optical path portion 41. The remote light source preferably has sufficient optical energy to provide high-intensity light that supports very short image exposure times (e.g., on the order of microseconds), such as a halogen lamp, an LED light engine, a super-continuum light source, a laser light source, a Xenon or Mercury arc lamp, Xenon flash lamp, or other types of flash lamps, or the like. In some embodiments, a remote light source may be power-controllable or shutter-controllable to deliver various controllable pulse lengths and/or colors, etc. Alternatively, the first light source 30a may be formed with a local light source such as an LED (rather than a remote light source). Optionally, one or more additional light source(s) 30a' may be used to provide a broader combined beam shape, or additional light intensity, or a different light characteristic than that of the first light source 30a (e.g., a different color).

The beam steering arrangement 50a generally includes at least one movable beam steering element 51, a controllable actuator 52 that moves the movable beam steering element 51 to selected positions, at least a first beam steering surface portion 54N (e.g., the surface portions 54NA-54NH in the embodiment shown in FIG. 2) that provides a first relatively narrow nominal divergence amount (e.g., corresponding to θN, defined in a plane including the optical axis 25) and/or angle of incidence range, and at least a second beam steering surface portion 54W that provides a second relatively wide nominal divergence amount (e.g., corresponding to θW, defined in a plane including the optical axis 25) and/or angle of incidence range, as described in greater detail below. In the illustrated embodiment, the first beam steering surface portion(s) 54N (in this case, 54NA-54NH) and the second beam steering surface portion(s) 54W are fixed to a support 55a proximate to the objective lens 23. In various embodiments, the light source 30a, the beam steering arrangement 50a, and the beam deflecting arrangement 38 may be fixed to a frame in an operable configuration around the objective lens 23 (e.g., the frame 58a, shown in FIG. 3). In various embodiments, the beam deflecting arrangement 38 and/or the first and second beam steering surface portion(s) 54N and 54W may be made from unitary molded reflective elements, or an assembly of elements, or according to other known optical component fabrication methods. In the various embodiments, the controllable actuator 52 may be made of a galvanometer, piezoelectric motor, miniature stepper or DC motor, or the like, and the movable beam steering element 51 includes a reflective (e.g., mirror) surface, to together form a controllable deflection mirror that controls the steering of the light beam received from the light source 30a.

As previously indicated, the second optical path portion 43 may comprise multiple segments. In the illustrated embodiment, it comprises a first ("unprimed") segment 43N or 43W between the movable beam steering element 51 and the first or second beam steering surface portions 54N or 54W, and a second ("primed") segment 43N' or 43W' between the first or second beam steering surface portions 54N or 54W and corresponding surface portions 38N or 38W of the beam deflecting arrangement 38. For example, three alternative second optical path portions comprising alternative first and second segments 43NA and 43NA', 43NH and 43NH', and 43W1 and 43W1', respectively, are illustrated in FIG. 2.

An example of operation, typical of when the field of view is to be illuminated with a relatively narrow angle of incidence range (e.g., corresponding to a first relatively narrow divergence amount ON) from a particular nominal angle of incidence, may be described with reference to an optical path including the movable beam steering element 51 and the particular set of corresponding surfaces portions 54NA, and 38NA. In this example, the movable beam steering element 51 is positioned to receive the light beam along the first optical path portion 41 and to steer the light beam along the first segment 43NA of the second optical path portion 43 to the first beam steering surface portion 54NA. The surface portion 54NA then deflects the light beam along the second segment 43NA' of the second optical path portion 43 to the surface portion 38NA of the beam deflecting arrangement 38, while providing or maintaining the relatively narrow divergence angle $\theta_N$ in a plane parallel to the optical axis 25 (e.g., the surface portions 54N may be shaped with relatively little curvature in planes including the optical axis 25.) As illustrated in FIG. 2, the first beam steering surface portion 54NA may be shaped such that it is curved in a plane that is generally perpendicular to the optical axis 25, which causes the light beam to diverge generally horizontally along the second segment 43NA' of the second optical path portion 43 to fill along the length of surface portion 38NA. For example, FIG. 2 illustrates three representative light rays output from the first beam steering surface portion 54NA diverging horizontally along the second segment 43NA' to illuminate the surface portion 38NA at three respective points $38NA_1$, $38NA_2$, and $38NA_3$. The surface portion 38NA receives the light beam along the second segment 43NA' of the second optical path portion 43 and deflects it along the third optical path portion 45NA where it forms a curved sheet-like light beam that converges approximately along a segment (e.g., a quadrant) of a cone, to illuminate the field of view from a first quadrant around the optical axis 25 at a corresponding nominal angle of incidence $\beta_{NA}$ over a relatively narrow angle of incidence range (e.g., corresponding to $\theta_N$).

As shown in FIG. 2 and described immediately above, the relatively narrow nominal divergence amount $\theta_N$ may be a first divergence amount that correspond to the light beam illuminating approximately a single one of the respective surface portions 38N (e.g., 38NA, 38NB, etc.) of the beam deflecting arrangement 38, such that the fast variable angle of incidence illumination configuration 100a illuminates the field of view 46 from a relatively narrow angle of incidence range about the respective nominal angle of incidence of a particular one of the respective surface portions 38N. In other words, the first nominal divergence amount $\theta_N$ results in a "narrow" or thin sheet-like light beam along the third optical path portion 45N illuminating the field of view 46. It will be understood that by appropriately positioning the movable beam steering element 51, similar illumination may be provided along analogous optical paths that include corresponding pairs of elements 54NX-38NX (where X represents one of the identifiers A-H) to provide similar "narrow angle of incidence range" illumination to the field of view 46 at other respective nominal angles of incidence $\beta_{NX}$. For example, FIG. 2 illustrates the central rays along an optical path 43H-54NH-43NH'-38NH-45NH, which provides illumination at the nominal angle of incidence $\beta_{NH}$. In some embodiments, the angle of incidence range corresponding to the first relatively narrow divergence amount $\theta_N$ may be at most 15 degrees, or 10 degrees, or less.

An example of operation, typical of when the field of view is to be illuminated with a relatively wide angle of incidence range (e.g., corresponding to a second relatively wide divergence amount θW), may be described with reference to an optical path including the movable beam steering element 51 and the set of corresponding surfaces portions 54W and 38W. In this example, the movable beam steering element 51 is positioned to receive the light beam along the first optical path portion 41 and to steer the light beam along the first segment 43W of the second optical path portion 43 to the second (type of) beam steering surface portion 54W. In the embodiment shown in FIGS. 2 and 3, the surface portion 54W may comprise a plurality of facets that are shaped to individually deflect the light beam along individual angles in the second segment 43W' of the second optical path portion 43 to individual ones of the surface portions 38W of the beam deflecting arrangement 38 (e.g., individual facets are curved in a plane that is generally perpendicular to the optical axis 25, and in a plane including the optical axis 25 are angled at an individual facet angle and are not individually significantly curved). Thus, as shown in FIG. 2, in combination, the light beam(s) from the set of facets of the surface portion 54W provide a relatively wide divergence angle θW in a plane parallel to the optical axis 25. The set of surface portions 38W, which are distributed to span most of the beam deflecting arrangement 38, receive the light beam(s) from the facets of the surface portion 54W over the relatively wide divergence angle θW along the second segment 43NA' of the second optical path portion 43 and deflect the light beam(s) along the third optical path portion 45NA to form a light beam that is distributed throughout a segment (e.g., a quadrant) of a cone, to illuminate the field of view from a first quadrant around the optical axis 25 over a relatively wide angle of incidence range (e.g., corresponding to θW and/or the angle of incidence range corresponding to the combined set of surface portions 38W). In various embodiments, the angle of incidence range corresponding to the second relatively wide divergence amount θW may span at least two of the nominal angles incidence provided by the surface portions 38N, or at least 30 degrees, or 45 degrees, or 60 degrees, or more.

It will be appreciated that for the illumination configuration 100a, switching between the narrow and wide ranges of angle of incidence, as well as the selection of a particular nominal angle of incidence for the narrow range of angle of incidence, can be made very fast based on the very small angular adjustments needed for the movable beam steering element 51, which may be made quite small and light (e.g., on the order of a few square millimeters in surface area). At the same time, a powerful concentrated light source (e.g., light conducted by optical fiber from a powerful remote light source) may be used. This combination of features may be essential in order to provide rapidly configurable strobe illumination that can provide images that effectively freeze the high speed motion that is desirable for increasing inspection throughput in various applications of general purpose precision machine vision inspection systems. It will be appreciated that in such high speed applications, not only is powerful strobe illumination important, it is just as important that very little time (e.g., on the order of microseconds or milliseconds) is allowed and/or used to reconfigure such illumination between images covering a sequence of locations (inspected features) on a work piece. Thus, the combination of illumination configuration features outlined above is particularly advantageous for such applications.

The illumination configuration outlined above is configured to allow maximization of the intensity (concentrated focus) and angular specificity of the illumination at the field of view 46. Therefore, because the surface portions 54N and 54W have different individual locations, their cooperating surface portions 38N and 38W also have different locations. However, it will be appreciated that in other embodiments, with some compromise in the above factors, the surface portion 54W may cooperate with the set of surface portions 38N, and the surface portions 38W may be omitted. Furthermore, in some embodiments, the surface portions 54N (and/or 38N, and/or 38W) may be less distinct and/or provided by portions of a continuous surface.

Two or more of the illumination configurations 100a may be provided to surround the objective lens 23, each for covering a section or quadrant of a generally circular illumination system around the optical axis 25. FIG. 3 shows two illumination configurations 100a' and 100a" for covering two opposite quadrants as part of four quadrants, though it should be apparent to those skilled in the art that the illumination space about the optical axis 25 can be divided into any number of sections, such as eight or more.

The illumination configuration 100a described in reference to FIGS. 2 and 3 is a single focal length design. That is, the illumination is approximately focused at a single location along the optical axis 25, coinciding with a focused field of view 46 for the objective lens 23. However, in some general purpose machine vision inspection systems that use interchangeable objective lenses, it may be desirable for an illumination configuration to provide approximately focused illumination at either of two locations along the optical axis 25, depending on the location of the focused field of view for various alternative objective lenses.

Figure 4:
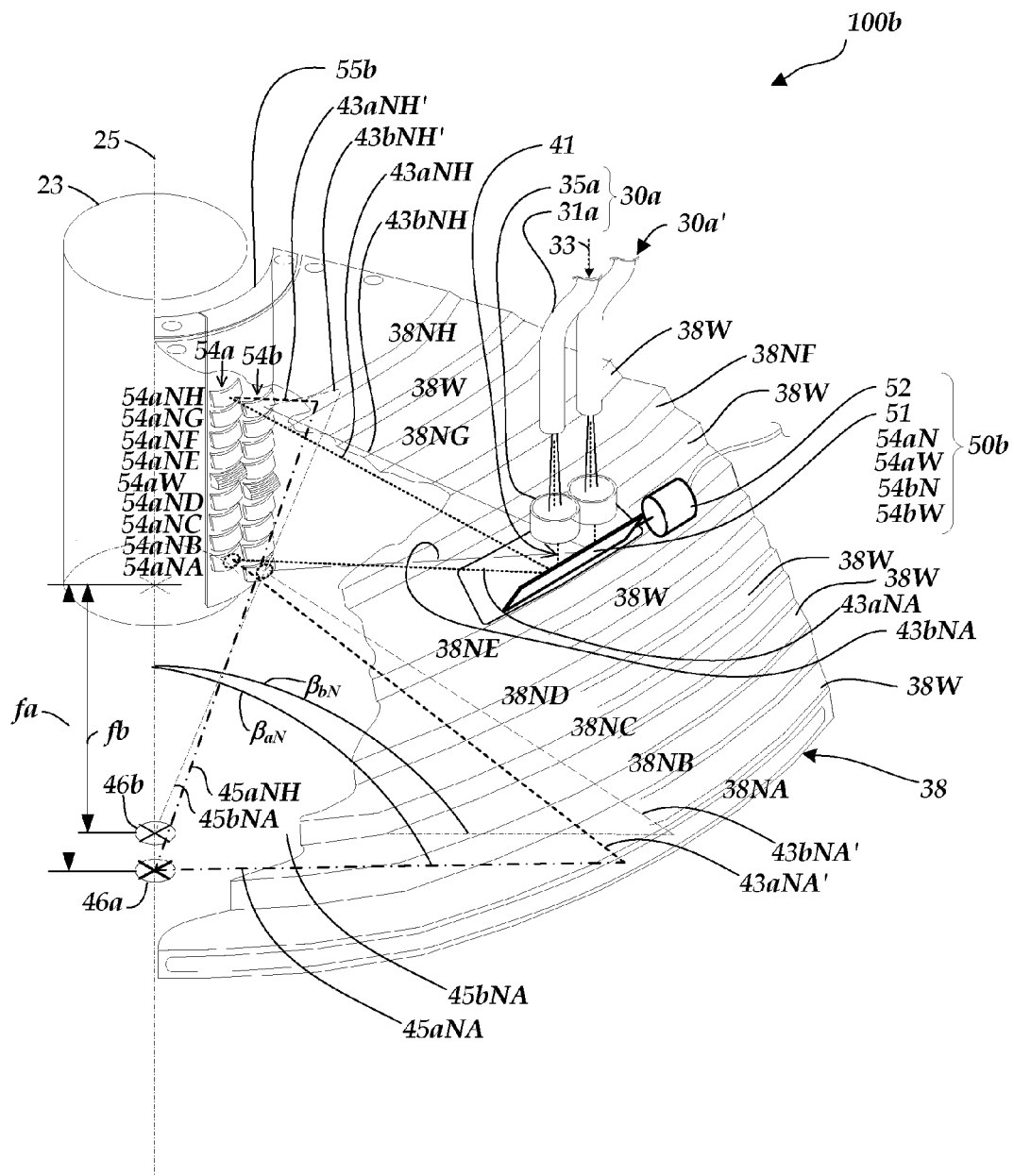
FIG. 4 is a perspective view, partially cut away, of an illumination configuration according to another embodiment of the present invention.

FIG. 4 illustrates another embodiment of the illumination configuration 100b, providing dual focal distances fa and fb along the optical axis 25, wherein various alternatives for the objective lens 23 may provide either of two different focused fields of views 46a and 46b, corresponding to the focal distances fa and fb, respectively. Elements that provide similar functions typically have similar reference number prefixes in FIGS. 2-8 (e.g., the element 54a or 54b in FIG. 4 is analogous to the counterpart element 54 in FIGS. 2 and 3, 50b in FIG. 4 is analogous to the counterpart element 50a in FIGS. 2 and 3, and so on). Furthermore, use of the previously described convention regarding the narrow and wide angle of incidence range indicators N and W is continued, and these will be understood to correspond to operation associated with a first narrow divergence angle (e.g., $θ_N$) or a second wide divergence angle (e.g., similar to $θ_w$, shown in FIG. 2), respectively, as previously described with reference to FIG. 2. The elements of the encoder configurations of FIGS. 4-8 may therefore be understood largely based on previous description of their analogous counterparts in FIGS. 1 and 2, unless otherwise indicated by description or context. Therefore, only certain aspects of the illumination configurations of FIGS. 4-8 are described in detail below.

The illumination configuration 100b shown in FIG. 4 operates similarly to the illumination configuration 100a, described above, except that it includes first and second light sources 30a and 30a', and the beam steering arrangement 50b includes the beam steering surface portions 54aN (54aNA-54aNH) and 54aW that are used with the light source 30a, as well as the beam steering surface portions 54bN (54bNA-54bNH) and 54bW that are used with the light source 30a'. The first and second sets of beam steering surface portions respectively receive the light beam from the first and second light sources 30a and 30a' and direct the light beam to the field of view on the first and second focal planes 46a and 46b, respectively.

An example of operation, typical of when the field of view 46a is to be illuminated at the focal distance fa with a relatively narrow angle of incidence range (e.g., corresponding to a first relatively narrow divergence amount θN) from a particular nominal angle of incidence, may be described with reference to an optical path including the first light source 30a, the movable beam steering element 51 and the particular set of corresponding surfaces portions 54aNA, and 38NA. In this example, the first light source 30a is on (the second light source 30a' is off), and the movable beam steering element 51 is positioned to receive the light beam from the first light source 30a along the first optical path portion 41 and to steer the light beam along the first segment 43aNA of the second optical path portion 43 to the first beam steering surface portion 54aNA. The surface portion 54aNA then deflects the light beam along the second segment 43aNA' of the second optical path portion 43 to the surface portion 38NA of the beam deflecting arrangement 38, while providing or maintaining a relatively narrow divergence angle in a plane parallel to the optical axis 25. The surface portion 38NA receives the light beam along the second segment 43aNA' of the second optical path portion 43 at a particular angle from the surface portion 54aNA, and as a result deflects it along the corresponding third optical path portion 45aNA where it forms a curved sheet-like light beam that converges approximately along a segment (e.g., a quadrant) of a cone, to illuminate the field of view 46a at the focal length fa at a corresponding nominal angle of incidence $\beta_{aNA}$ (shown generically as $\beta_{aN}$) over a relatively narrow angle of incidence range. It will be understood by analogy with previous description that by appropriately positioning the movable beam steering element 51 to aim the light beam at the various first (type) beam steering surface portions 54aX, illumination may be provided at the focal distance fa at other respective nominal angles of incidence $\beta_{aNX}$, or by aiming the light beam at the second (type) beam steering surface portion 54aW, illumination may be provided at the focal distance fa over a wide angle of incidence range.

An example of operation, typical of when the field of view 46b is to be illuminated at the focal distance fb with a relatively narrow angle of incidence range (e.g., corresponding to a first relatively narrow divergence amount ON) from a particular nominal angle of incidence, may be described with reference to an optical path including the second light source 30a', the movable beam steering element 51 and the particular set of corresponding surfaces portions 54bNA, and 38NA. In this example, the second light source 30a' is on (the first light source 30a is off), the movable beam steering element 51 is positioned to receive the light beam from the first light source 30a' along the first optical path portion 41 and to steer the light beam along the first segment 43bNA of the second optical path portion 43 to the first beam steering surface portion 54bNA. The surface portion 54bNA then deflects the light beam along the second segment 43bNA' of the second optical path portion 43 to the surface portion 38NA of the beam deflecting arrangement 38, while providing or maintaining a relatively narrow divergence angle in a plane parallel to the optical axis 25. The surface portion 38NA receives the light beam along the second segment 43bNA' of the second optical path portion 43 at a particular angle from the surface portion 54bNA. Since this particular angle is different than that provided by the surface portion 54aNA in the previous example of operation, as a result the surface portion 38NA deflects it along a corresponding third optical path portion 45bNA where it forms a curved sheet-like light beam that converges approximately along a segment (e.g., a quadrant) of a cone, to illuminate the field of view 46b at the focal length fb at a corresponding nominal angle of incidence $\beta_{bNA}$ (shown generically as $\beta_{bN}$) over a relatively narrow angle of incidence range. It will be understood by analogy with previous description that by appropriately positioning the movable beam steering element 51 to aim the light beam at the various first (type) beam steering surface portions 54bX, illumination may be provided at the focal distance fb at other respective nominal angles of incidence $\beta_{bNX}$, or by aiming the light beam at the second (type) beam steering surface portion 54bW, illumination may be provided at the focal distance fb over a wide angle of incidence range.

In the illustrated embodiment, the two light sources 30a, 30a' are individually aligned such that the same movable beam steering element 51 and controllable actuator 52 are used for all operations. However, it is also possible to provide independent separate movable beam steering element 51 and controllable actuator 52 for each light source, or to use a movable beam steering element that is controllable in two axes to appropriately steer a light beam from a single light source to any of the surface portions 54aN, 54aW, 54bN or 54bW. It should be apparent to one skilled in the art that further embodiments are possible that allow illumination of the field of view 46 located at three or more focal planes.

Figure 5:
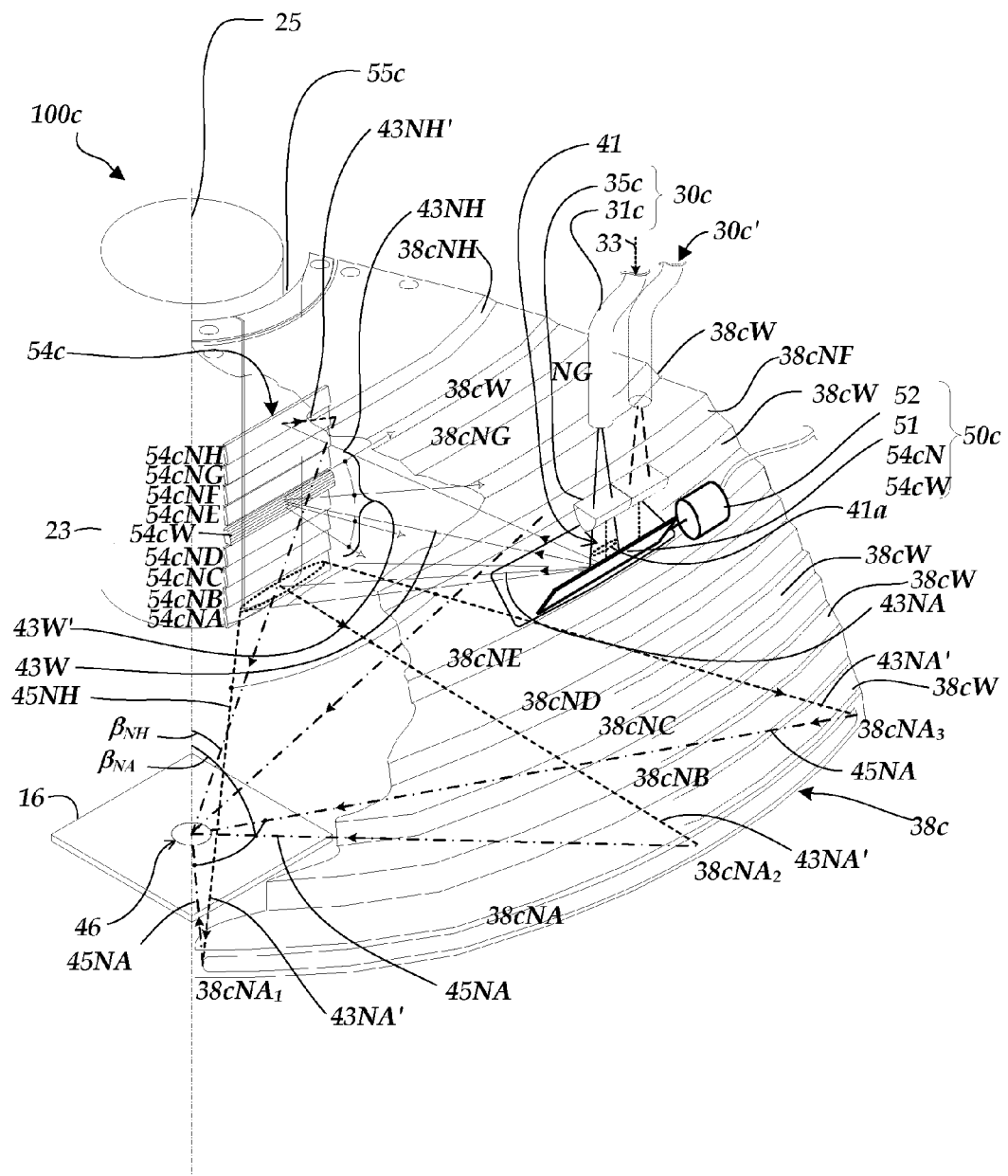
FIG. 5 is a perspective view, partially cut away, of an illumination configuration according to yet another embodiment of the present invention.

FIG. 5 illustrates yet another embodiment of the illumination configuration 100c constructed in accordance with the present invention. Briefly, the illumination configuration 100c shown in FIG. 5 operates similarly to the illumination configuration 100a, described above, except for two main differences. Firstly, the light source 30c includes a cylindrical lens 35c rather than a circular lens. Therefore, the "non-focusing plane" of the cylindrical lens 35c allows the light beam to continue to diverge in one plane along the first optical path portion 41 and along the first segment 43NX (e.g., 43NA) of the second optical path portion 43 to a first or second beam steering surface portion 54cNX (e.g., 54cNA) or 54cW. Secondly, the first and second beam steering surface portions 54cNX and 54cW are shaped to cooperate with the wider light beam that results from the aforementioned divergence allowed by the cylindrical lens 35c (e.g., see the beam spot shown in dashed outline on the first surface portion 54cNA in FIG. 5). In the embodiment shown in FIG. 5, the first and second beam steering surface portions 54cNX and 54cW are wider, and may be less curved in a plane perpendicular to the optical axis 25, in comparison to their counterparts in FIG. 2. It will be understood that the curvature of the surface portions 38cNX and 38cW of the beam deflecting arrangement 38c may adjusted (relative to its previously described counterparts) in light of the aforementioned light beam differences, to provide the desired illumination focus at the field of view 46.

One advantage of the illumination configuration 100c is that it conveniently allows the light beams from multiple light sources, which may be arranged side by side (e.g., as shown for the two light sources 30c and 30c' in FIG. 5), to overlap along substantially the same optical paths using relatively simple optical elements and without complex alignment. Such light sources may be operated simultaneously for enhanced intensity, and/or individually for enhanced spectrum choices. This may be particularly advantageous in embodiments that use local LED light sources instead of the light sources 30c and/or 30c' (which may use powerful remote light generators), since multiple LED's may be need to be combined to provide desirable light intensities.

Figure 6:
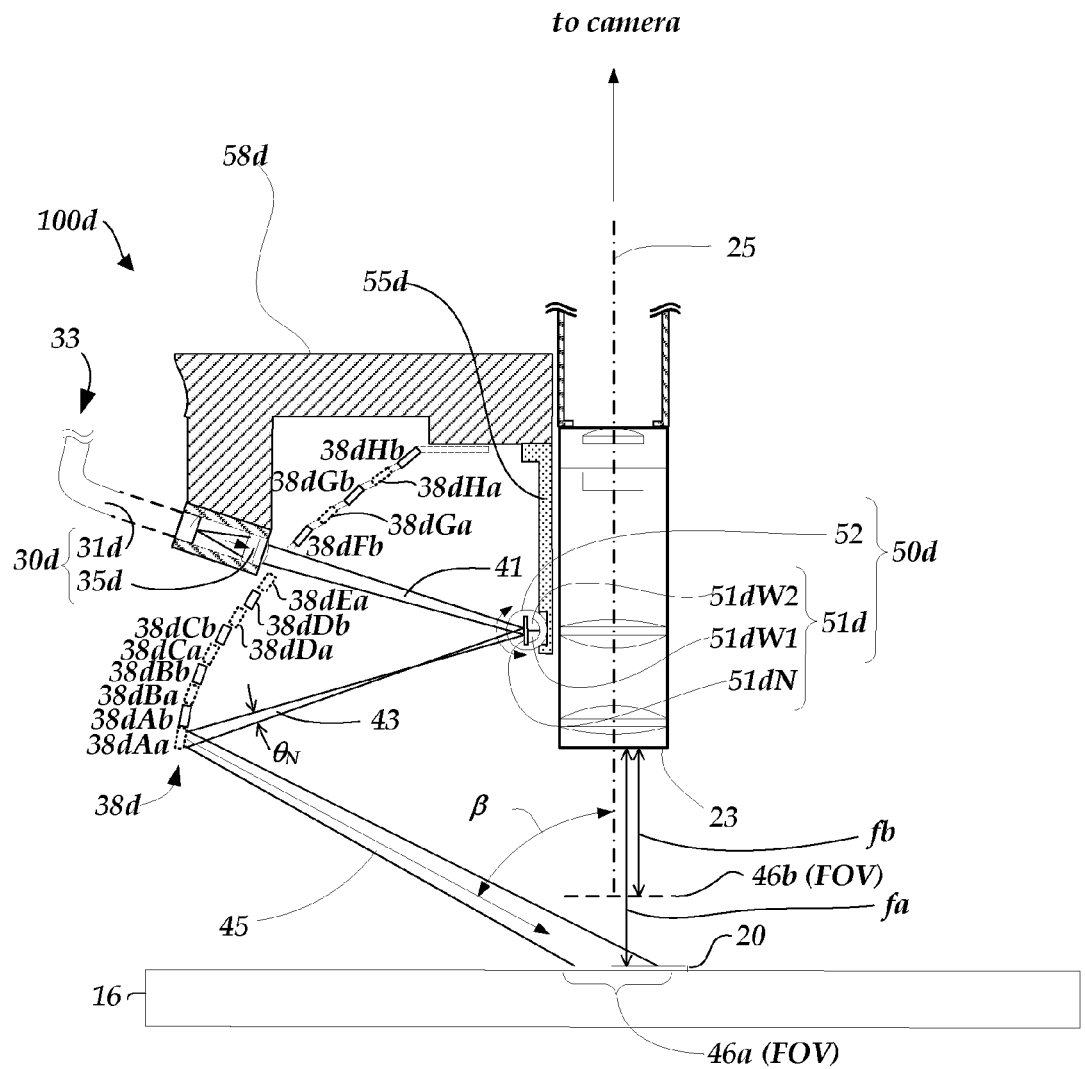
FIG. 6 is a cross-sectional view provided for one quadrant of an illumination configuration according to a further embodiment of the present invention.

FIG. 6 illustrates a further alternative embodiment of the illumination configuration 100d formed in accordance with the present invention. While not illustrated, the same illumination configuration 100d as shown in a "1st quadrant" may be provided in the opposite quadrant in a minor image, and/or in additional quadrants or segments around the objective lens 23, as described for previous embodiments. Briefly, the illumination configuration 100d shown in FIG. 6 is a "dual focal length" design that operates similarly to the illumination configurations described above, except for two primary differences. A first difference is in the configuration of the beam steering arrangement 50d relative to its previously described counterparts. A second difference is in the beam deflecting arrangement 38d, which as a result of the changes in the beam steering arrangement 50d omits special wide angle of incidence range surface portions (e.g., comparable to 38W in previous embodiments), but provides a set of surface portions 38dXa that provide a first illumination focal length fa, and a set of surface portions 38dXb that provide a second illumination focal length fb, (where X represents one of the identifiers A-H), as described in greater detail below. In the embodiment shown in FIG. 6, surface portions of the element 38d do not include the N and W designators shown in previous embodiments, because in this embodiment each surface portion may participate in providing both type of illumination (at different times), as described in greater detail below.

As shown in FIG. 6, similarly to previous embodiments, the beam steering arrangement 50d includes a movable beam steering element 51d and a controllable actuator 52. However, in the present embodiment 50d, the movable beam steering element 51d directly steers the light beam to the elements 38dXa or 38dXb as described in greater detail below, and it includes a first (type) beam steering surface portion 51dN for producing narrow angle of incidence range illumination and also two second (type) beam steering surface portions 51dW1, 51dW2 for producing wide angle of incidence range illumination. The element 54 (or its counterparts, 54a, etc.), included in previous embodiments, is therefore omitted.

An example of operation, typical of when the field of view 46a is to be illuminated at the focal distance fa with a relatively narrow angle of incidence range (e.g., corresponding to a first relatively narrow divergence amount θN) from a particular nominal angle of incidence, may be described with reference to an optical path including the first light source 30d, the movable beam steering element 51d and the particular surfaces portion 51dN, and 38dAa. In this example, the movable beam steering element 51d is positioned such that the first beam steering surface portion 51dN receives the light beam from the first light source 30a along the first optical path portion 41 and steers the light beam along the second optical path portion 43 to the surface portion 38dAa of the beam deflecting arrangement 38d, while providing or maintaining a relatively narrow divergence angle θN in a plane parallel to the optical axis 25. The surface portion 38dAa receives the light beam along the second optical path portion 43 at a particular angle from the surface portion 51dN, and as a result deflects it along the corresponding third optical path portion 45 where it forms a curved sheet-like light beam that converges approximately along a segment (e.g., a quadrant) of a cone, to illuminate the field of view 46a at the focal length fa at a corresponding nominal angle of incidence βaNA (shown generically as β) over a relatively narrow angle of incidence range, similarly to previously described embodiments. It will be understood by analogy with previous description that by appropriately positioning the movable beam steering element 51d to aim the light beam from first beam steering surface portion 51dN at the various surface portions 38dXa (where X represents one of the identifiers A-H), narrow angle of incidence range illumination may be provided at the focal distance fa at other respective nominal angles of incidence βaNX. Alternatively, to provide wide angle of incidence range illumination at the focal distance fa, the movable beam steering element 51d may be rotated or positioned such that the second beam steering surface portion 51dW1 receives the light beam from the first light source 30a along the first optical path portion 41 and steers the light beam along the second optical path portion 43 with a wide divergence angle in a plane parallel to the optical axis 25 (e.g., similar to the wide divergence angle θW shown in FIG. 2) to each of the surface portions 38dAa-38dHa of the beam deflecting arrangement 38d. The light beams from the combination of surface portions 38dAa-38dHa then combine to provide the wide angle of incidence range illumination at the focal distance fa.

It will be understood that analogous operations may be used when the field of view 46b is to be illuminated at the focal distance fb except, in the case of providing narrow angle of incidence range illumination the first beam steering surface portion 51dN is positioned to steer the light beam along the second optical path portion 43 to a surface portion 38dAb of the beam deflecting arrangement 38d, and in the case of providing wide angle of incidence range illumination the second beam steering surface portion 51dW2 is positioned to receive the light beam along the first optical path portion 41 and steer the light beam along the second optical path portion 43 with a wide divergence angle to each of the surface portions 38dAb-38dHb of the beam deflecting arrangement 38d. In one embodiment, the first beam steering surface portion 51dN may have a shape analogous to that previously described for the first beam steering surface portions 54N shown in FIG. 2 (e.g., the surface portion 51dN may be shaped with relatively little curvature in a plane including the optical axis 25 and curved in a plane that is generally perpendicular to the optical axis 25) such that the light beam diverges horizontally along the second optical path portion 43 to fill along the length of surface portions 38dXa or 38dXb. The second beam steering surface portion 51dW1 or 51dW2 may have a shape analogous to that previously described for the second beam steering surface portion 54W shown in FIG. 2. For example, the second beam steering surface portion 51dW1, may comprise curved facets arranged at various facet angles as needed to simultaneously direct light beams to fill a plurality of the surface portions 38dXa (or similarly for the second beam steering surface portion 51dW2 and the surface portions 38dXb). As previously indicated, in some embodiments the surface portions 38dXa (and/or 38dXb) may be formed such that they are not readily distinguishable from one another and/or are part of continuously curved surface. In some embodiments, the second beam steering surface portion 51dW1 (or 51dW2) may comprise a continuously curved surface that provides the wide divergence angle, rather than distinguishable facets. In some embodiments, the illumination configuration 100d may be configured such that the second beam steering surface 51dW2 is omitted and the second beam steering surface portion 51dW1 may be positioned to provide wide angle of incidence illumination for either of the focal lengths fa or fb. It should be apparent to one skilled in the art that further embodiments are possible that allow illumination of the field of view 46 at 3 or more focal lengths, or that if illumination is desired at a single focal length then the surface portions 51dW2 and 38dXb may be omitted.

Figure 7:
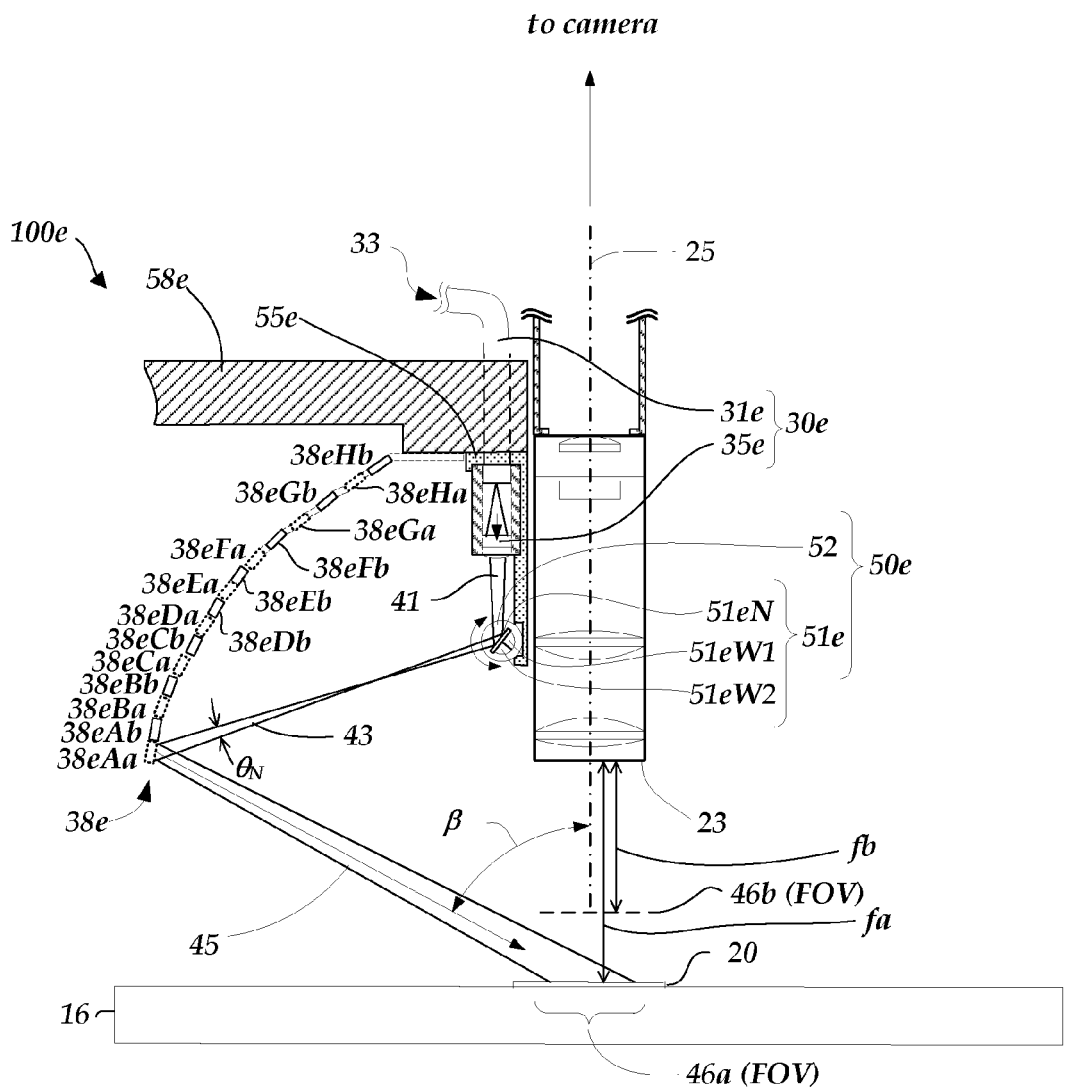
FIG. 7 is a cross-sectional view provided for one quadrant of an illumination configuration according to a still further embodiment of the present invention.

FIG. 7 illustrates yet another embodiment of the illumination configuration 100e formed in accordance with the present invention. This embodiment may be understood to operate similarly to the previously described embodiment of FIG. 6, except for the location of the light source 30e. Specifically, with the light source 30e being provided close to the objective lens 23 in the present embodiment, it becomes unnecessary for the light source 30e and/or the first optical path portion 41 to extend through the beam deflecting arrangement 38e. Therefore, in contrast to the embodiment of FIG. 6, the beam deflecting arrangement 38e may include a set of "uninterrupted" respective surface portions 38eXa and 38eXb, which may simplify fabrication and assembly, and enhance the uniformity of the illumination provided. While not illustrated, the same illumination configuration 100e as shown in the "1st quadrant" may be provided in the opposite quadrant in a minor image, and/or in other segments or quadrants around the objective lens 23, similar to previously described embodiments.

Figure 8:
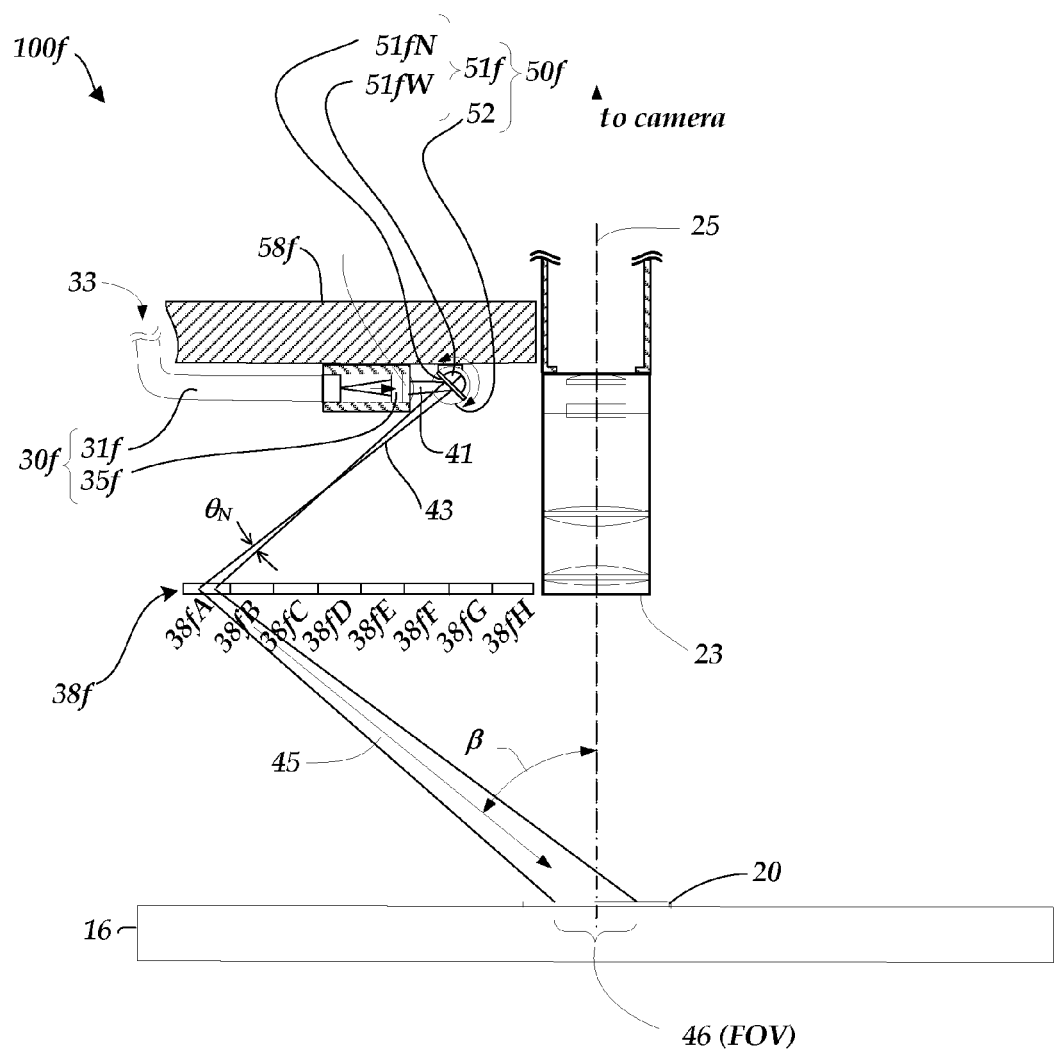
FIG. 8 is a cross-sectional view provided for one quadrant of an illumination configuration according to a different embodiment of the present invention.

FIG. 8 illustrates yet another embodiment of the illumination configuration 100f formed in accordance with the present invention. This embodiment may be understood to operate similarly to the previously described embodiment of FIG. 7, except in this embodiment the plurality of respective surface portions 38fA-38fH of the beam deflecting arrangement 38f are refractive or diffractive, not reflective (e.g., in one embodiment the beam deflecting arrangement 38f may comprise relatively flat Fresnel-like diffractive lens surface portions.) Briefly, when the field of view 46 is to be illuminated with a relatively narrow angle of incidence range from a particular nominal angle of incidence, the movable beam steering element 51f is positioned such that the first beam steering surface portion 51fN receives the light beam from the first light source 30f along the first optical path portion 41 and steers the light beam along the second optical path portion 43 to a surface portion 38fX (where X represents one of the identifiers A-H) of the beam deflecting arrangement 38f, while providing or maintaining a relatively narrow divergence angle ON in a plane parallel to the optical axis 25. The surface portion 38fX receives the light beam along the second optical path portion 43 and deflects it along the corresponding third optical path portion 45 where it forms a curved sheet-like light beam that converges approximately along a segment (e.g., a quadrant) of a cone, to illuminate the field of view 46 at a nominal angle of incidence βNX (shown generically as β) over a relatively narrow angle of incidence range, similarly to previously described embodiments. Alternatively, to provide wide angle of incidence range illumination, the movable beam steering element 51f may be rotated or positioned such that the second beam steering surface portion 51fW receives the light beam from the first light source 30f along the first optical path portion 41 and steers the light beam along the second optical path portion 43 with a wide divergence angle in a plane parallel to the optical axis 25 (e.g., similar to the wide divergence angle θW shown in FIG. 2) to each of the surface portions 38fA-38fH of the beam deflecting arrangement 38f. The light beams from the combination of surface portions 38fA-38fH then combine to provide the wide angle of incidence range illumination.

The embodiment shown in FIG. 8 is a single focal length design. However, it should be apparent to one skilled in the art that further embodiments are possible that allow illumination of the field of view 46 at two or more focal lengths. For example, one such embodiment may include a refractive or diffractive beam deflecting arrangement 38f with alternating surface portions 38fX that provide different focal lengths, in a manner analogous to the alternating reflective surface portions 38eXa and 38eXb shown in FIG. 7. While not illustrated, the same illumination configuration 100f as shown in the "1st quadrant" may be provided in the opposite quadrant in a mirror image, and/or in other segments or quadrants around the objective lens 23, similar to previously described embodiments.

While illustrative embodiments have been illustrated and described, it will be appreciated that various changes can be made therein without departing from the spirit and scope of the invention.

The embodiments of the invention in which an exclusive property or privilege is claimed are defined as follows:

1. A fast variable angle of incidence illumination configuration for use in a machine vision inspection system comprising at least a first objective lens having an optical axis, the fast variable angle of incidence illumination configuration comprising:
   (a) a first light source configured to direct a light beam along a first optical path portion;
   (b) a beam steering arrangement configured to receive the light beam along the first optical path portion and steer the light beam along a second optical path portion; and
   (c) a beam deflecting arrangement comprising a plurality of respective surface portions arranged at respective nominal angles of incidence relative to the optical axis, the beam deflecting arrangement configured to receive the light beam along the second optical path portion and deflect the light beam along a third optical path portion to illuminate a field of view of the objective lens, wherein:
the beam steering arrangement of (b) comprises:
   (i) at least one movable beam steering element and a controllable actuator that moves the movable beam steering element;
   (ii) at least a first beam steering surface portion that provides a first nominal divergence amount for the light beam along the second optical path portion, the divergence amount defined in a plane including the optical axis; and
   (iii) at least a second beam steering surface portion that provides a second nominal divergence amount for the light beam along the second optical path portion, the divergence amount defined in a plane including the optical axis, the first nominal divergence amount corresponds to the light beam illuminating approximately a single respective surface portion of the beam deflecting arrangement such that the fast variable angle of incidence illumination configuration illuminates the field of view from a narrow range of angles corresponding to the respective nominal angle of incidence of that single respective surface portion, the second nominal divergence amount corresponds to the light beam illuminating at least two respective surface portions of the beam deflecting arrangement such that the fast variable angle of incidence illumination configuration illuminates the field of view from a broader range of angles that is broader than the narrow range of angles and that includes the respective nominal angles of incidence of the at least two respective surface portions, and the beam steering arrangement is configured to provide the light beam along the second optical path portion with the first nominal divergence amount to different respective surface portions of the beam deflecting arrangement to illuminate the field of view from the narrow range of angles at a first time, and is configured to provide the light beam along the second optical path portion with the second nominal divergence amount to the at least two respective surface portions of the beam deflecting arrangement to illuminate the field of view from the broader range of angles at a second time.

2. The illumination configuration of claim 1, wherein the first and second beam steering surface portions are reflective.

3. The illumination configuration of claim 2, wherein the respective surface portions of the beam deflecting arrangement are reflective.

4. The illumination configuration of claim 2, wherein the respective surface portions of the beam deflecting arrangement are refractive.

5. The illumination configuration of claim 1, wherein the beam steering arrangement comprises a fixed element that receives the light beam from the movable beam steering element and outputs the light beam along the second optical path portion.

6. The illumination configuration of claim 5, wherein the fixed element comprises a plurality of different beam steering surface portions, and different beam steering surface portions output the light beam along the second optical path portion to different respective surface portions of the beam deflecting arrangement.

7. The illumination configuration of claim 6, wherein the fixed element comprises the first and second beam steering surface portions and the movable beam steering element comprises a third beam steering surface portion that directs the light beam to different ones of the first and second beam steering surface portions.

8. The illumination configuration of claim 7, wherein the at least one first beam steering surface portion that provides the first nominal divergence amount comprises a plurality of beam steering surface portions that provide the first nominal divergence amount, and different beam steering surface portions that provide the first nominal divergence amount output the light beam along the second optical path portion to different respective surface portions of the beam deflecting arrangement.

9. The illumination configuration of claim 7, wherein the at least one second beam steering surface portion that provides the second nominal divergence amount comprises a beam steering surface portion defining a plurality of facets that respectively output the light beam along the second optical path portion to a plurality of respective surface portions of the beam deflecting arrangement.

10. The illumination configuration of claim 6, wherein the plurality of different beam steering surface portions comprise first and second sets of different beam steering surface portions, wherein:

the first set of different beam steering surface portions is configured to output the light beam along the second optical path portion to different respective surface portions of the beam deflecting arrangement such that different respective surface portions of the beam deflecting arrangement deflect the light beam along the third optical path portion to illuminate the field of view of the objective lens at a first distance along the optical axis from the objective lens; and the second set of different beam steering surface portions is configured to output the light beam along the second optical path portion to different respective surface portions of the beam deflecting arrangement such that different respective surface portions of the beam deflecting arrangement deflect the light beam along the third optical path portion to illuminate the field of view of the objective lens at a second distance along the optical axis from the objective lens.

11. The illumination configuration of claim 6, wherein each of the plurality of different beam steering surface portions has a curvature along the direction generally perpendicular to the optical axis so that the light beam output therefrom diverges along the second optical path portion.

12. The illumination configuration of claim 6, wherein each of the plurality of different beam steering surface portions has an elongate dimension along the direction generally perpendicular to the optical axis so that the light beam output therefrom has an expanded width.

13. The illumination configuration of claim 1, wherein the movable beam steering element comprises the first and second beam steering surface portions.

14. The illumination configuration of claim 13, wherein the first beam steering surface portion comprises a generally flat surface and the second beam steering surface portion comprises a generally semispherical surface.

15. The illumination configuration of claim 13, wherein the plurality of respective surface portions of the beam deflecting arrangement comprise first and second sets of respective surface portions, wherein:

the first set of respective surface portions is configured to output the light beam along the third optical path portion to illuminate the field of view of the objective lens at a first distance along the optical axis from the objective lens; and the second set of respective surface portions is configured to output the light beam along the third optical path portion to illuminate the field of view of the objective lens at a second distance along the optical axis from the objective lens.

* * * * *